United States Patent
Garwood et al.

(10) Patent No.: US 11,231,476 B2
(45) Date of Patent: Jan. 25, 2022

(54) ACCELERATED MAGNETIC RESONANCE IMAGING ACQUISITION USING TWO-DIMENSIONAL PULSE SEGMENTS AS VIRTUAL RECEIVERS

(71) Applicant: REGENTS OF THE UNIVERSITY OF MINNESOTA, Minneapolis, MN (US)

(72) Inventors: Michael Garwood, Minneapolis, MN (US); Michael Mullen, Minneapolis, MN (US); Alexander Gutierrez, Minneapolis, MN (US); Jarvis Haupt, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 0 days.

(21) Appl. No.: 16/859,177

(22) Filed: Apr. 27, 2020

(65) Prior Publication Data
US 2020/0341096 A1 Oct. 29, 2020

Related U.S. Application Data

(60) Provisional application No. 62/839,067, filed on Apr. 26, 2019.

(51) Int. Cl.
*G01R 33/561* (2006.01)
*G01R 33/48* (2006.01)
(Continued)

(52) U.S. Cl.
CPC ......... *G01R 33/5612* (2013.01); *A61B 5/055* (2013.01); *G01R 33/3635* (2013.01);
(Continued)

(58) Field of Classification Search
CPC ............ G01R 33/5612; G01R 33/4824; G01R 33/5608; G01R 33/5616; G01R 33/3635;
(Continued)

(56) References Cited

U.S. PATENT DOCUMENTS

| 7,075,301 B2 * | 7/2006 | Zhu ..................... G01R 33/3415 324/309 |
| 2008/0100292 A1 * | 5/2008 | Hancu .................. G01R 33/246 324/307 |

(Continued)

OTHER PUBLICATIONS

Griswold et al., Generalized Autocalibrating Partially Parallel Acquisitions (GRAPPA), Magnetic Resonance in Medicine, 2002, 47(6):1202-1210.

(Continued)

*Primary Examiner* — Susan S Lee
(74) *Attorney, Agent, or Firm* — Quarles & Brady LLP

(57) ABSTRACT

Accelerated data acquisition using two-dimensional ("2D") radio frequency ("RF") pulse segments as virtual receivers for a parallel image reconstruction technique, such as GRAPPA, is provided. Data acquisition is accelerated using segmented RF pulses for excitation, refocusing, or both, and undersampling k-space along a dimension of the RF pulse segments. In this way, parallel image reconstruction techniques, such as GRAPPA, can be adapted to work with a single RF receive coil. By undersampling the data acquisition and finding correlations between the data from different segments, unsampled data can be recovered. This shortens scan times, yielding the advantages of segmented pulses without the formerly required long scans.

18 Claims, 8 Drawing Sheets

(51) Int. Cl.
 *A61B 5/055* (2006.01)
 *G01R 33/56* (2006.01)
 *G01R 33/36* (2006.01)

(52) U.S. Cl.
 CPC ..... *G01R 33/4824* (2013.01); *G01R 33/5608* (2013.01); *G01R 33/5616* (2013.01)

(58) Field of Classification Search
 CPC ... G01R 33/482; G01R 33/5611; A61B 5/055; A61B 5/0205; A61B 5/0803; A61B 5/33
 See application file for complete search history.

(56) References Cited

U.S. PATENT DOCUMENTS

2013/0134975 A1* 5/2013 Nehrke ............ G01R 33/5659
 324/309
2016/0245882 A1* 8/2016 Popescu ............ G01R 33/5611

OTHER PUBLICATIONS

Jang et al., 2D Pulses Using Spatially Dependent Frequency Sweeping, Magnetic Resonance in Medicine, 2016, 76 (5): 1364-1374.

Mullen et al., Two-Dimensional Frequency-Swept Pulse with Resilience to Both B1 and B0 Inhomogeneity, Journal of Magnetic Resonance, 2019, 299:93-100.

Orzada et al., RF Excitation Using Time Interleaved Acquisition of Modes (TIAMO) to Address B1 Inhomogeneity in High-Field MRI, Magnetic Resonance in Medicine, 2010, 64(2):327-333.

Panych et al., Selection of High-Definition 2D Virtual Profiles with Multiple RF Pulse Excitations Along Interleaved Echo-Planar k-Space Trajectories, Magnetic Resonance in Medicine, 1999,41 (2):224-229.

Pruessmann et al., SENSE: Sensitivity Encoding for Fast MRI, Magnetic Resonance in Medicine, 1999, 42 (5):952-962.

* cited by examiner

ACCELERATED MAGNETIC RESONANCE IMAGING ACQUISITION USING TWO-DIMENSIONAL PULSE SEGMENTS AS VIRTUAL RECEIVERS

CROSS-REFERENCE TO RELATED APPLICATIONS

This application claims the benefit of U.S. Provisional Patent Application Ser. No. 62/839,067, filed on Apr. 26, 2019, and entitled "ACCELERATED MAGNETIC RESONANCE IMAGING ACQUISITION USING TWO-DIMENSIONAL PULSE SEGMENTS AS VIRTUAL RECEIVERS," which is herein incorporated by reference in its entirety.

STATEMENT REGARDING FEDERALLY SPONSORED RESEARCH

This invention was made with government support under EB025153, EB015894, and EB008389 awarded by the National Institutes of Health. The government has certain rights in the invention.

BACKGROUND

Large magnetic field inhomogeneity ($\Delta B_0$) can be a significant cause of spatial flip-angle variation when using ordinary, limited-bandwidth RF pulses. Multidimensional RF pulses are particularly sensitive to inhomogeneity due to their extended pulse length, which decreases their bandwidth.

Previous work has shown how the k-space trajectory of a multidimensional RF pulse can be segmented and acquired in separate shots. In the absence of segmenting, multidimensional RF pulses suffer from a low bandwidth due to the long pulse lengths necessary for full sampling. Undersampling of excitation k-space permits a shorter pulse length and increased pulse bandwidth; however, in MRI applications of segmented 2D and 3D pulses, the need to fully sample acquisition k-space per excitation segment leads to longer scans, since the imaging time increases linearly with the number of pulse segments used. The latter decreases the utility of this approach.

Signals produced by each excitation segment contain independent information since the same object is being imaged while using the same transmit and receive coil(s). This is due to various spatial phases resulting per excitation with the different pulse segments.

Segmenting multidimensional pulses is useful whenever multidimensional localization is desired with robustness to $B_0$ inhomogeneity. Examples include localized spectroscopy and inner volume imaging. For sequences with an EPI readout, the reduced field-of-view ("FOV") resulting from using a multidimensional pulse permits shorter echo-trains, thereby diminishing distortions in regions with large susceptibility differences. Segmenting the excitation pulse in these cases could increase the excitation bandwidth, yielding a more robust excitation profile.

SUMMARY OF THE DISCLOSURE

The present disclosure addresses the aforementioned drawbacks by providing a method for generating an image of a subject using a magnetic resonance imaging (MRI) system. The method includes selecting with a computer system, a radio frequency (RF) pulse. The RF pulse is then segmented in order to generate a series of RF pulse segments. Data are acquired from a subject using an MRI system implementing a pulse sequence that includes the series of RF pulse segments. An image of the subject is then reconstructed from the acquired data using a reconstruction technique that treats the series of RF pulse segments as virtual receivers.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

BRIEF DESCRIPTION OF THE DRAWINGS

FIG. 2A shows the RF amplitude as a function of k-space, FIG. 2B shows the RF phase as a function of k-space, and FIG. 2C shows the transverse magnetization profile produced by the RF pulse.

FIG. 3A is an example of a single segment coverage of k-space. FIG. 3B is an example of covering k-space in two segments, with each sampling 14 equidistant lines of k-space. FIG. 3C is an example of a 7-segment trajectory, with each segment sampling 4 equidistant lines of k-space. FIG. 3D is an example of a fully segmented trajectory, in which only one line of k-space is sampled with each segment.

FIG. 7A shows an image obtained with the sequence as described run with a non-selective excitation and FOV=192×192×192 mm$^3$ and matrix size of 192×192×192. The red box indicates the zoomed FOV in the phase-encoded dimensions. FIG. 7B shows an image obtained from a reconstruction using the fully sampled dataset. FIG. 7C shows an image obtained from a reconstruction using only the undersampled data, resulting in low resolution due to the center ACS region containing most of the signal energy. FIG. 7D shows an image obtained from a GRAPPA reconstruction. FIG. 7E shows a retrospective undersampling pattern. White indicates sampled values, whereas black indicates unsampled values.

FIG. 8A shows an image obtained with the sequence as described run with a non-selective excitation and FOV=192×192×192 mm$^3$ and matrix size of 192×192×192. The red box indicates the zoomed FOV in the phase-encoded dimensions. FIG. 8B shows an image obtained from a reconstruction using the fully sampled dataset. FIG. 8C shows an image obtained from a reconstruction using only the undersampled data, resulting in low resolution due to the center ACS region containing most of the signal energy. FIG. 8D shows an image obtained from a GRAPPA reconstruction. FIG. 8E shows a retrospective undersampling pattern. White indicates sampled values, whereas black indicates unsampled values

DETAILED DESCRIPTION

Figure 1:
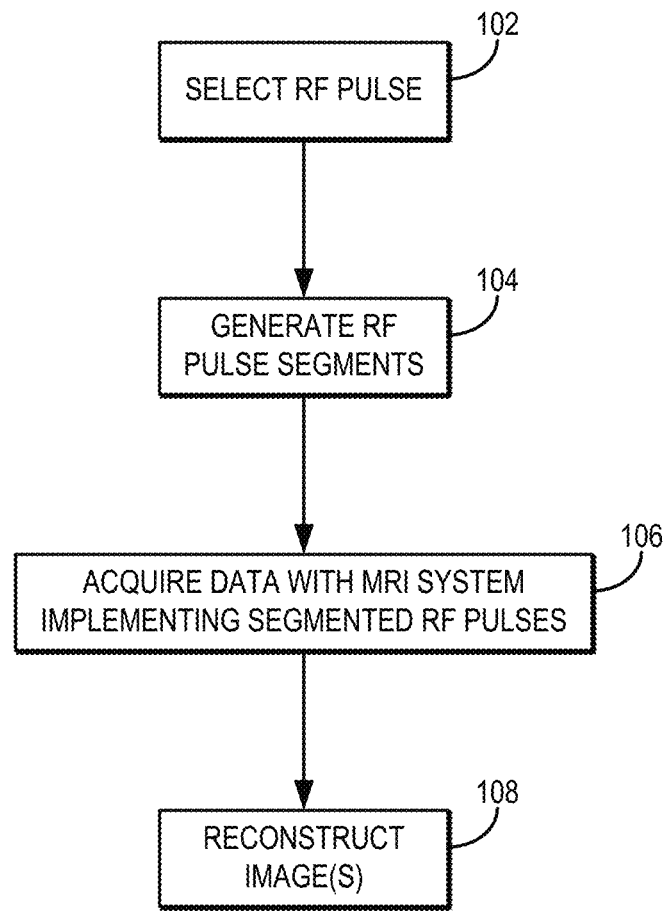
FIG. 1 is a flowchart setting forth the steps of an example method for generating an image with an MRI system using one or more segmented RF pulses and by reconstructing an image using the RF pulse segments as virtual receivers.

Described here are systems and methods for accelerated image acquisition using two-dimensional ("2D") radio frequency ("RF") pulse segments as virtual receivers for a parallel image reconstruction technique, such as GRAPPA. Data acquisition is accelerated using segmented RF pulses for excitation, refocusing, or both. In this way, parallel image reconstruction techniques, such as GRAPPA, can be adapted to work with a single RF receive coil. By undersampling the data acquisition and finding correlations between the data from different segments, unsampled data can be recovered. This shortens scan times, yielding the advantages of segmented pulses without the formerly required long scans.

In addition to general imaging techniques (e.g., those using T1-weighted gradient-recalled echo pulse sequences, or other general imaging sequences), accelerated data acquisitions according to embodiments described in the present disclosure can be used to improve inner volume spectroscopy. In these instances, partial volume effects can be avoided because RF pulse shapes can be designed to have sharp boundaries. For example, when generating metabolite maps in the brain, lipids in the scalp can create a very strong signal that can bleed into the brain metabolite signal. Currently, planar saturation techniques are used in an attempt to spoil the lipid signal, but those approaches aren't always effective. Using the methods described in the present disclosure, RF pulses can be designed to have sharper boundaries such that these lipid signals do not bleed into the brain metabolite signal.

As another example, the methods described in the present disclosure can be used to accelerate other imaging techniques, such as B1-gradient based imaging methods. One non-limiting example of such techniques that can be accelerated using the methods described in the present disclosure is rotating frame zeugmatography ("RFZ"). In general, RFZ generates a gradient in the RF excitation field (i.e., the B1 field) in order to cause a variation in flip angle that corresponds to spatial locations along the B1-field gradient. This B1-field gradient can be used to provide spatial encoding of the magnetic resonance signals. The different (e.g., incremented) RF pulse lengths in RFZ can be used as RF pulse segments discussed in the present disclosure. In this way, RFZ can be accelerated (e.g., by omitting some pulse increments) and the mathematical framework described in the present disclosure used to provide advantages of reduced scan time without a corresponding loss in image quality.

As still another example, the methods described in the present disclosure can also provide improvements for dental imaging applications. In these instances, like the brain metabolite imaging application above, the lipids in the cheek can create a strong undesirable signal. Thus, by defining sharper boundaries for the RF pulses, signals from these lipids bleeding into the desired imaging region or volume can be mitigated.

As another similar example, the methods described in the present disclosure can provide benefits for imaging near metallic implants. In general, imaging near metallic implants is difficult because the metal in the implants can cause strong off resonances that result in signal loss. Using the methods described in the present disclosure, high bandwidth can be used to compensate for perturbations to $B_0$ around the implant.

In previous work, the acquired data for all pulse segments were fully sampled prior to a weighted, complex summation of the data. Using the systems and methods described in the present disclosure, the redundant information from acquisitions of different pulse segments can be used to undersample acquisition k-space even when using a single receive coil. For instance, the redundancy between pulse segments permits data undersampling in the phase-encoded dimension aligned with the segmented dimension of the pulse. Data can be recovered, for instance, by treating each readout as originating from a virtual receiver in a GRAPPA-type, or other suitable parallel imaging, reconstruction. This approach is made possible by treating the data from each pulse segment as if received by a virtual coil with a spatially dependent sensitivity map. The total number of virtual coils is then equal to the number of excitation segments used, provided there is only one receive coil.

One previous approach to accelerate an acquisition when using more than one type of excitation was a technique named Time Interleaved Acquisition of Modes ("TIAMO"). There, the transmit coil was driven in two different excitation modes, with the data being undersampled on acquisition for both modes and reconstructed using GRAPPA. This resulted in two virtual receive coils. This differs from the methods described in the present disclosure, in which the transmit coil is able to operate in the same excitation mode for all pulses, instead of using undersampled pulse segments for additional spatial encoding to accelerate data acquisition. The systems and methods described in the present disclosure also permit a zoomed FOV in two dimensions.

For instance, when using a segmented 2D RF pulse to increase bandwidth, the FOV can also be reduced in the two spatially-selected dimensions. Here, the different pulse segments induce unique spatial modulation with every excitation. The data from each excitation segment are then used to synthesize unsampled data in an accelerated acquisition. This concept is motivated by considering the excitation profile following a given pulse segment and the signal received following that excitation. Assuming a small tip angle excitation, the excitation profile $P_j(\vec{r})$ of the imaged object $I(\vec{r})$ following pulse segment j is given by, $$P_j(\vec{r}) \propto i\gamma I(\vec{r}) \int_0^{T_p} B_{1,j}^+(\vec{r}, t)\exp(i\vec{r}\cdot\vec{k}_j(t))dt; \quad (1)$$

where $B_{1,j}^+(\vec{r},t)$ is the total complex RF field at position $\vec{r}$ and time t, $\gamma$ is the proton gyromagnetic ratio, $T_p$ is the RF pulse duration, and $\vec{k}_j(t)$ is a parameterized trajectory through excitation k-space for pulse segment j. The index j runs from $1, \ldots, N_s$, where $N_s$ is the number of pulse segments used. Assuming the transmit field is separable in space and time, that is, $B_{1,j}^+(\vec{r},t) = B_{1,j}^+(\vec{r})B_{1,k}^+(t)$, Eqn. (1) can be rewritten as, $$P_j(\vec{r}) \propto i\gamma I(\vec{r})B_{1,j}^+(\vec{r})\int_0^{T_p} B_{1,j}^+(t)\exp(i\vec{r}\cdot\vec{k}_j(t))dt \quad (2).$$

The result of the integral is a function of position only, so Eqn. (2) can be rewritten as, $$P_j(\vec{r}) \propto i\gamma I(\vec{r})B_{1,j}^+(\vec{r})M_j(\vec{r}) \quad (3);$$

where $$M_j(\vec{r}) \triangleq \int_0^{T_p} B_{1,j}^+(t)\exp(i\vec{r}\cdot\vec{k}_j(t))dt \quad (4).$$

Consider the signal, $S_{m,j}$, received in coil m following excitation by pulse segment j during signal acquisition. The index m is in the range $1, \ldots, N_c$, where $N_c$ is the number of physical coils used. When using a spatially dependent receive field $B_1^-(\vec{r})$, the signal can be written as, $$S_{m,j}(\vec{k}_a(t)) \propto \int_V B_{1,m}^-(\vec{r})P_j(\vec{r})\exp(-i\vec{r}\cdot\vec{k}_a(t))d\vec{r} \quad (5).$$

The subscript a denotes acquisition, and the integral is performed over the sensitive volume V of the receive coil. Inserting the definition of $P_j$ from Eqn. (3), the signal is recast as, $$S_{m,j}(\vec{k}_a(t)) \propto i\gamma\int_V B_{1,m}^-(\vec{r})M_j(\vec{r})B_{1,j}^+(\vec{r})I(\vec{r})\exp(-i\cdot\vec{r}\cdot\vec{k}_a(t))d\vec{r} \quad (6).$$

By defining a spatially dependent quantity as, $$\tilde{B}_{m,j}(\vec{r}) \triangleq i\gamma B_{1,j}^+(\vec{r})B_{1,m}^-(\vec{r})M_j(\vec{r}) \quad (7);$$

the signal equation becomes, $$S_{m,j}(\vec{k}_a(t)) \propto \int_V \tilde{B}_{m,j}(r)\tilde{I}(\vec{r})\exp(-i\cdot\vec{r}\cdot\vec{k}_a(t))d\vec{r}. \quad (8).$$

From Eqns. (7) and (8), the quantity $\tilde{B}_{m,j}$ can be interpreted as a complex coil sensitivity profile. Here, the virtual coil profile is the product of the physical receiver sensitivity, transmit field map, and pulse segment excitation profile. This is distinct from other methods, which have treated the composite receive sensitivity as the product of the physical receive sensitivity and transmit field map only. When only one physical receive coil is present, there are still $N_s$ virtual coils to work with. When an $N_s$-segment pulse is combined with standard GRAPPA, the data from each pulse segment acquired with one physical coil can be split into $N_s$ virtual coil data sets. Hence, the number of effective coils, $\tilde{N}_c$, is equal to the product $N_sN_c$, as seen from Eqn. (7).

When using segmented pulses with N segments the signal-to-noise ratio ("SNR") for an N-segment RF pulse with respect to a single-shot pulse with N averages decreases as:

$$\frac{SNR_{segmented}}{SNR_{single-shot}} = \frac{\sum_{j=1}^{N}|C_j|}{\sqrt{N\sum_{j=1}^{N}|C_j|^2}}; \quad (9)$$

with $C_j$ defined as $$C_j = \max|\int_0^T(t)\exp(-i\phi_{RF,j}(t))\exp(i\vec{r}\cdot\vec{k}_j(t))dt| \quad (10);$$

where the subscript j denotes segment number and i is the square root of −1. The $C_j$ are weighting coefficients used in the pulse segment combination. In Eqn. (10), each $C_j$ is set equal to the maximum value of the integral across all space r, but other scaling prescriptions could alternatively be used, such as the mean value of each segment's magnetization profile.

When partially segmenting a 2D pulse, the flip angle at each spatial location varies from segment to segment, and the amount of variation is spatially dependent and increases with number of segments used, except when using the fully segmented pulse. With the commonly employed condition $TR \ll T_1$, it may not be possible to ignore variable $T_1$-weighting of the different segments. The coefficients $C_j$ can therefore be used to scale the peak RF amplitude to obtain a more consistent flip angle across pulse segments. This procedure utilizes a processing step to compensate for the increased flip angles from scaling, so that signal outside the region of interest is perfectly cancelled when summing over segments. By scaling the amplitude of each pulse segment, flip angle variations can be minimized enough to avoid noticeable image artifacts.

As noted, when based on a k-space description, 2D RF pulses can be applied in segments to increase the excitation bandwidth relative to a single-shot implementation, at a cost of increased imaging time. The increased imaging time can be overcome by undersampling the acquisition in one phase-encoded dimension. Data from each segment are viewed as originating from "virtual receive coils" rather than multiple physical coils. The undersampled data are reconstructed using parallel imaging techniques (e.g., GRAPPA).

The segmented RF pulses may have a high bandwidth in a fast time direction and a low bandwidth in a slow time direction, in which the pulses are segmented. Segmenting the RF pulse requires fewer gradient blips, or no gradient blips in the fully segmented case where every k-space line is a separate acquisition. To increase the bandwidth in the slow time direction, however, segmenting the RF pulse k-space in multiple undersampled segments can be used to increase their bandwidth by shortening pulse length.

Additionally or alternatively, real-time adjustments of voltage can be made to compensate for B1+ maps and to keep the flip angle constant. For instance, 2D frequency-swept RF pulses can be modified to compensate for B1+ inhomogeneities. Similarly, fully segmenting the pulse's k-space yields significant immunity to B0 inhomogeneities.

Referring now to FIG. 1, a flowchart is illustrated as setting forth the steps of an example method for generating an image with an MRI system using one or more segmented RF pulses and by reconstructing an image using the RF pulse segments as virtual receivers.

The method includes selecting an RF pulse with a computer system, as indicated at step 102. In general, selecting the RF pulse can include selecting a desired RF pulse profile, or other characteristics of the RF pulse, to achieve the desired effect (e.g., excitation, refocusing) over a prescribed region or volume. The RF pulse profile is, for example, a two-dimensional ("2D") RF pulse profile. Preferably, the RF pulse profile defines a frequency-swept RF pulse, which enables higher bandwidth in the fast-selected dimension. As one example, the RF pulse profile may be a 2D hyperbolic secant pulse (e.g., an HS1 pulse). Other frequency-swept pulses can also be used, including higher order HSn pulses or a chirp pulse.

Figures 2A, 2B, 2C:
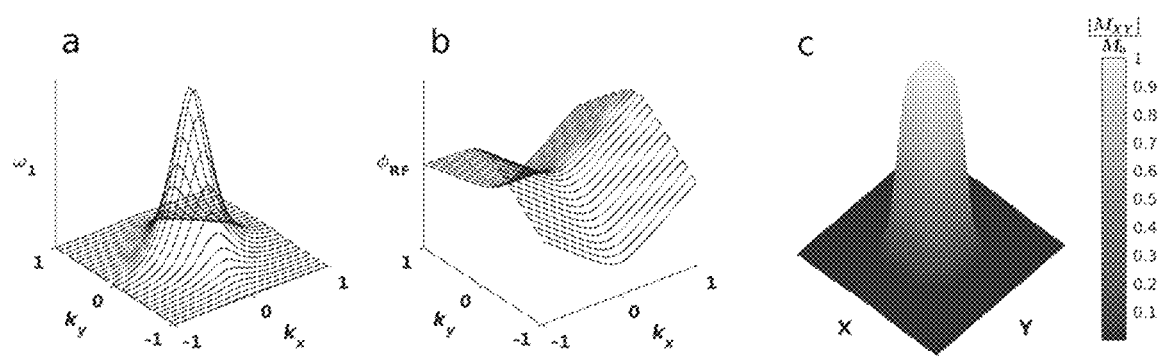
FIGS. 2A-2C illustrate a k-space description of an example 2D RF pulse.

As noted, in one example, a 2D RF pulse which is a hyperbolic secant pulse in both dimensions in k-space can be used. FIGS. 2A-2C illustrate a k-space description of such a 2D RF pulse. FIG. 2A shows the RF amplitude as a function of k-space, FIG. 2B shows the RF phase as a function of k-space, and FIG. 2C shows the transverse magnetization, $M_{xy}$, profile produced by this pulse.

Denoting a normalized k-space vector by $\kappa_{f,s} \in [-1,1]$ in the fast and slow dimensions, respectively, the amplitude-modulated and phase-modulated functions of the RF pulse, as defined in terms of the pulse's k-space trajectory, are, $$\omega_1 = \omega_{1,max} \operatorname{sec} h(\beta \kappa_f(t)) \operatorname{sec} h(\beta \kappa_s(t)) \quad (11);$$

$$\phi_{RF} = A_f \log(\cos h(\beta \kappa_f(t))) \pm A_s \log(\cos h(\beta \kappa_s(t))) \quad (12).$$

In these equations, $\beta$ determines where these functions are truncated. As one non-limiting example, the value of $\beta$ can be determined according to sec $h(\beta)=0.01$ (i.e., the amplitude-modulated function truncates at one percent of maximum). In Eqn. (12), choosing the positive sign leads to a parabolic phase over the object, while a negative sign yields a hyperbolic phase profile. In the example implementations described below, it is assumed that the negative sign is used. Additionally, $\kappa_{f,s}$ are normalized by, $$\kappa_{\{f,s\},max} = \frac{\gamma}{2} \left| \int G_{f,s}(t')dt' \right|. \quad (13)$$

Denoting the time-bandwidth product of the pulse in the fast and slow dimensions as $R_f$ and $R_s$, respectively, the coefficients $A_{f,s}$ can be defined by, $$A_{f,s} = \frac{\pi R_{f,s}}{2\beta}. \quad (14)$$

The formulae given yield a rectangular excitation profile, although the same trajectory can be used with other k-space weightings to obtain other excitation profiles, such as a circular excitation profile. Profile thickness is given in both dimensions of the current pulse as, $$\Delta x_{f,s} = \frac{R_{f,s}}{2k_{\{f,s\},max}}; \quad (15)$$

where f and s denote the fast and slow dimensions, respectively. For B1 compensation, the instantaneous vertex position is given by, $$x_{f,s}(t) = \frac{\Delta x_{f,s}}{2} \kappa_{f,s}(t). \quad (16)$$

As described below, Eqn. (16) can be used to modify the pulse to produce a uniform flip angle with a spatially-varying RF field, B1+. While the 2D spatial selection can be performed in any orientation, the fast and slow spatially-selected dimensions will herein generally be referred to as X and Y, respectively.

Because a 2D HS1 RF pulse is phase modulated in two spatial domains, 2D spatiotemporal excitation takes place during the pulse in a manner that is dictated by the resulting (rasterized) trajectory of a hyperbolic phase function in space. By assuming excitation at a given moment is localized to the vertex of this hyperbolic phase function, the 2D pulse can be modified to achieve uniform flip angle despite the existence of significant B1+ inhomogeneity. The process includes obtaining a unitless B1+ map (denoted by $B_{1,c}^+$) that is normalized to 1 at its maximum. Then the RF waveform can be recalculated as, $$\omega_{1,c}(t) = \frac{\omega_1(t)}{B_{1,c}^+(x_f(t), x_s(t))}; \quad (17)$$

where $x_f$ and $x_s$ describe the vertex position in the fast and slow dimensions, respectively. In areas where the $B_1^+$ map is not well defined, the original pulse value may be used.

After it is selected, the RF pulse is segmented to generate RF pulse segments, as indicated at step 104. The bandwidth in the slow-selected dimension can be increased by sampling segments of the fully sampled RF pulse with each excitation. Segmenting the RF pulse in this manner decreases the pulse length while maintaining the time-bandwidth product, such that the bandwidth in the slow dimension increases in inverse proportion to the pulse length reduction. To retain the desired 2D excitation profile, a full image readout can be acquired for each pulse segment. Depending on the specific sequence used, this might necessitate a tradeoff between minimum scan time and pulse bandwidth, since as the pulse is shortened, the minimum repetition time ("TR") decreases.

For a fixed TR, the total number of readouts to be acquired scales linearly with the number of pulse segments used. At the end of all acquisitions, the data can be summed over all segments in either k-space or image space with the appropriate weights, as described below.

Using a 2D pulse permits increased spatial resolution in a fixed imaging time by decreasing the field-of-view ("FOV") in the phase-encoded dimensions. By segmenting the pulse with a fixed TR, the acquisition time increases multiplicatively with the number of segments. Thus, to avoid increasing imaging time, the number of segments used can be selected so as not to exceed the acceleration gained by shrinking the FOV. As an example, assuming that phase encoding is performed in zoomed spatial dimensions (e.g., using a zoomed FOV), then the number of segments, $N_{seg}$, can be selected to satisfy, $$N_{seg} \leq \frac{PE_{1,full}}{PE_{1,zoomed}} \frac{PE_{2,full}}{PE_{2,zoomed}}; \quad (18)$$

to not increase the imaging time, where $PE_{i,full}$ and $PE_{i,zoomed}$ denote the number of phase encoded steps in a given dimension, i, in the full and zoomed FOV, respectively. This example assumes equal resolution between zoomed and full FOV scans.

To sample each segment correctly in pulse k-space, care should be taken to ensure that each segment has the same k-space center defined. Because the k-space trajectory is defined by the integral of the remaining gradient, there should be a variable area gradient lobe at the end of each segment in the slow-selected dimension. If these refocusing lobes are not the correct magnitude and polarity, different segments may amount to sampling the pulse multiple times along the same line(s) of k-space. Hence, the trajectory of a given segment can be influenced by the refocusing gradient, whereas the sampling weight is influenced by the RF amplitude and phase. Thus, even though each RF pulse segment can use the same gradient waveform during RF transmission, its trajectory in k-space is determined by the gradient refocusing lobe that follows the RF pulse.

As one non-limiting example, and referring to FIGS. 3A-3D, a 2D HS1 pulse was generated using 28 lines of k-space in the slow dimension (i.e., the y-direction). The time-bandwidth product ("TBP") was set to 9 and the slab thickness to 5 cm in both dimensions of the pulse. Each subpulse element was 700 µs long. The duration of the gradient blips in the slow dimension were 120 µs with a half-sinusoid shape. Taken together with the number of lines of k-space, these parameters fully define the 2D pulse according to Eqns. (11)-(13).

Figures 3A, 3B, 3C, 3D:
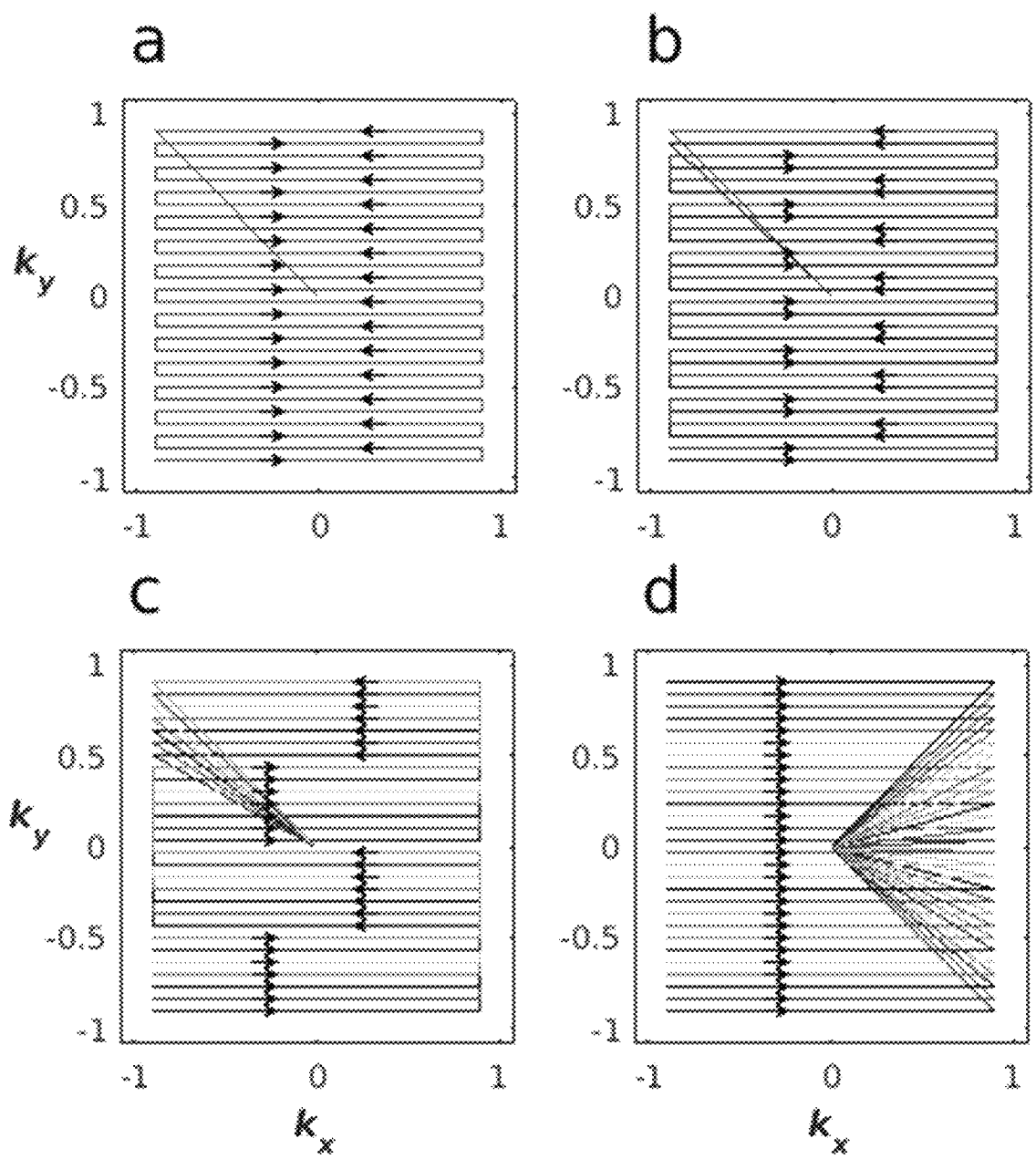
FIGS. 3A-3D show examples of k-space lines corresponding to a segmented 2D HS1 RF pulse.

FIG. 3A is an example of a single segment coverage of k-space. FIG. 3B is an example of covering k-space in two segments, with each sampling 14 equidistant lines of k-space. FIG. 3C is an example of a 7-segment trajectory, with each segment sampling 4 equidistant lines of k-space. FIG. 3D is an example of a fully segmented trajectory, in which only one line of k-space is sampled with each segment. The segmented RF pulses can optionally employ an autocalibrating signal ("AC S") region, which may be a rectangular ACS region, to maximize the acceleration gained.

Another option for the segmented RF pulses is to alternate the initial direction of the k-space trajectory between segments, which gives different off-resonant behavior. Trajectories do not need to be interleaved as shown. Segmented trajectories which sample k-space sequentially and do not overlap are also possible.

In some instances, a larger dimension can be chosen in the segmented (i.e., slow) direction of the 2D pulse, which has the spatial encoding information. In some other instances, a square region can be used to increase the number of points available for the kernel weight calibration.

Figure 4:
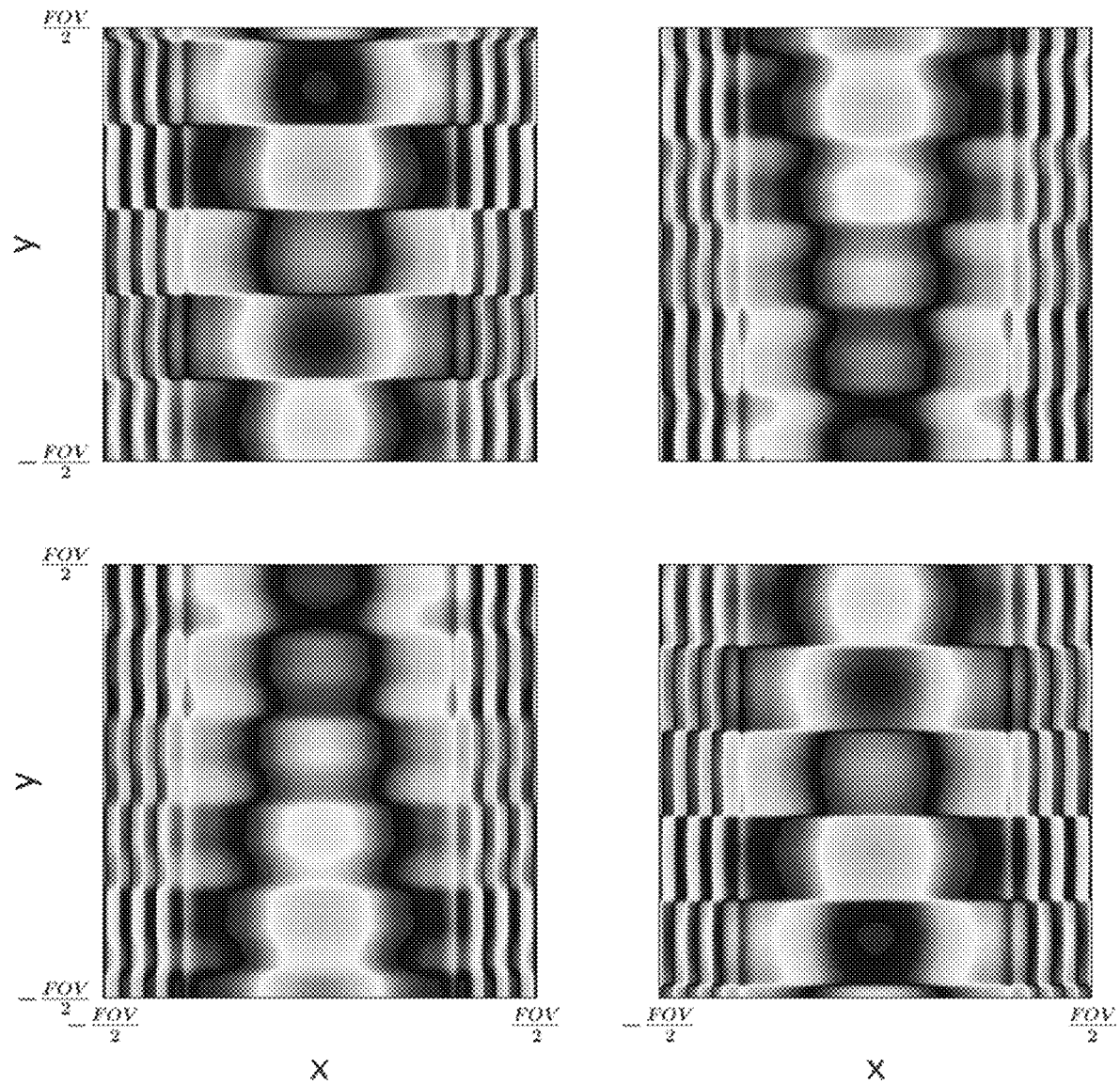
FIG. 4 illustrates the phase of the transverse magnetization for each of the 2D pulse segments corresponding to a 2D HS1 RF pulse when traversed in 4 segments.
Figure 5:
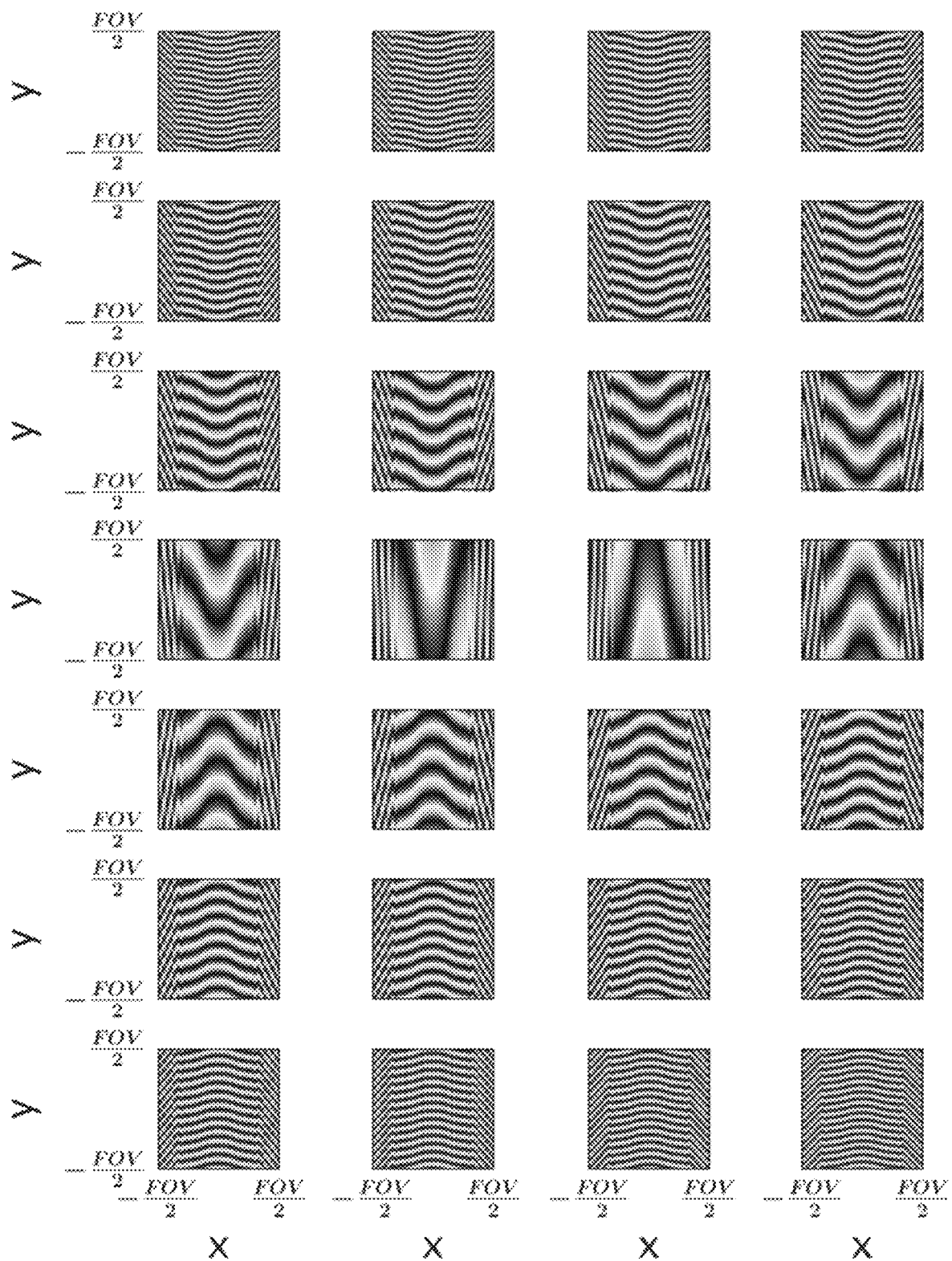
FIG. 5 illustrates the phase of the transverse magnetization for each of the 2D pulse segments corresponding to a 2D HS1 RF pulse when fully segmented into 28 segments. The x dimension is the fast (unsegmented) dimension of the pulse, while y is the slow (segmented) dimension of the pulse.
Figures 6A, 6B, 6C, 6D, 6E, 6F, 6G, 6H:
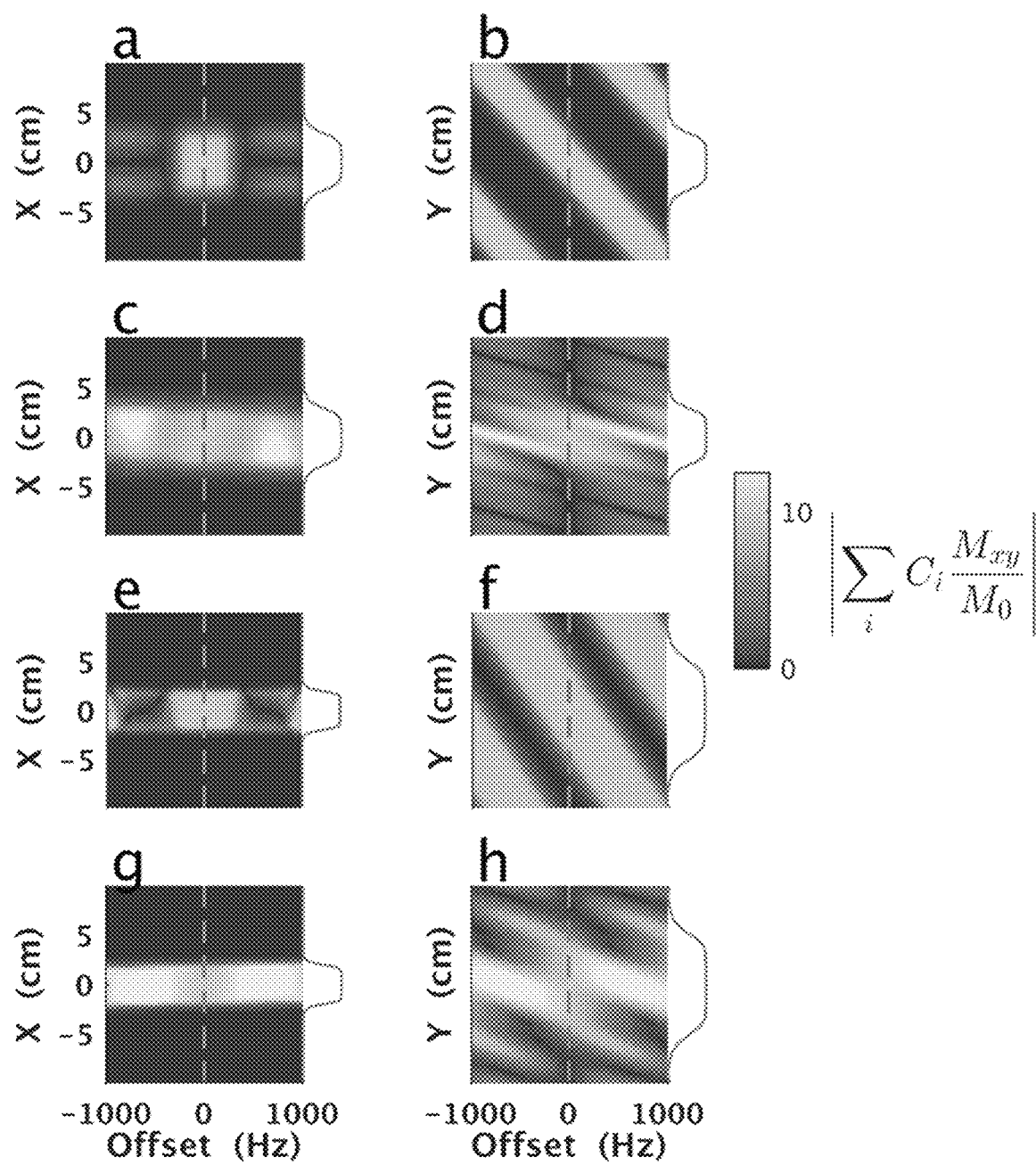
FIGS. 6A-6H show simulated excitation profiles produced by the 2D pulses used in experiments at 4T (FIGS. 6A-6D) and 3T (FIGS. 6E-6H), when performed without (FIGS. 6A, 6B, 6E, and 6F) and with segmentation (FIGS. 6C, 6D, 6G, and 6H). In all cases, the relative magnitude of the transverse magnetization is displayed as a function of position (e.g., x or y) versus resonance offset, for the case of flip angle equal 10° on resonance. As can be seen, the shape of the on-resonance excitation profile (green) is invariant with pulse segmentation. Coefficients used in combining the data from the 4 shots (segmented pulses) are described below.

Based on the example described above, FIG. 4 illustrates the real component of the transverse magnetization for each of the 2D pulse segments when traversed in 4 segments, and FIG. 5 illustrates the real component of the transverse magnetization for each of the 2D pulse segments when fully segmented into 28 segments.

The segmented RF pulses are then sent to the MRI system and implemented in one or more pulse sequences in order to acquire data, as indicated at step 106. In general, the segmented RF pulses are implemented in selected pulse sequence (e.g., for excitation, refocusing, or both) and data are acquired responsive to the applied, segmented RF pulses.

As one non-limiting example, the 2D HS1 RF pulse described above was used in a 3D-GRE sequence for an example imaging study. Both a fully segmented (i.e., 28 segments) and 4-segment RF excitation were used for comparison, with T1- and T2*-weighting, respectively. Sequence parameters were as follows.

To evaluate off-resonance effects for both 4-segment pulses used in experiments, the excitation profiles were simulated over a range of constant frequency offsets using an in-house Bloch simulator. These results are presented in FIGS. 6A-6H. The excitation profile in the fast dimension (x) of the pulse is clearly improved, while this is not evident in the slow dimension (y) of the pulse. For the 4-segment pulse used at 3T, the behavior in the slow dimension of the pulse is worse than for the 4-segment pulse at 4T due to using a lower $k_{max}$ in the slow dimension of the pulse, by nearly a factor of two. This leads to a higher sensitivity to off-resonance effects.

Figures 7A, 7B, 7C, 7D, 7E:
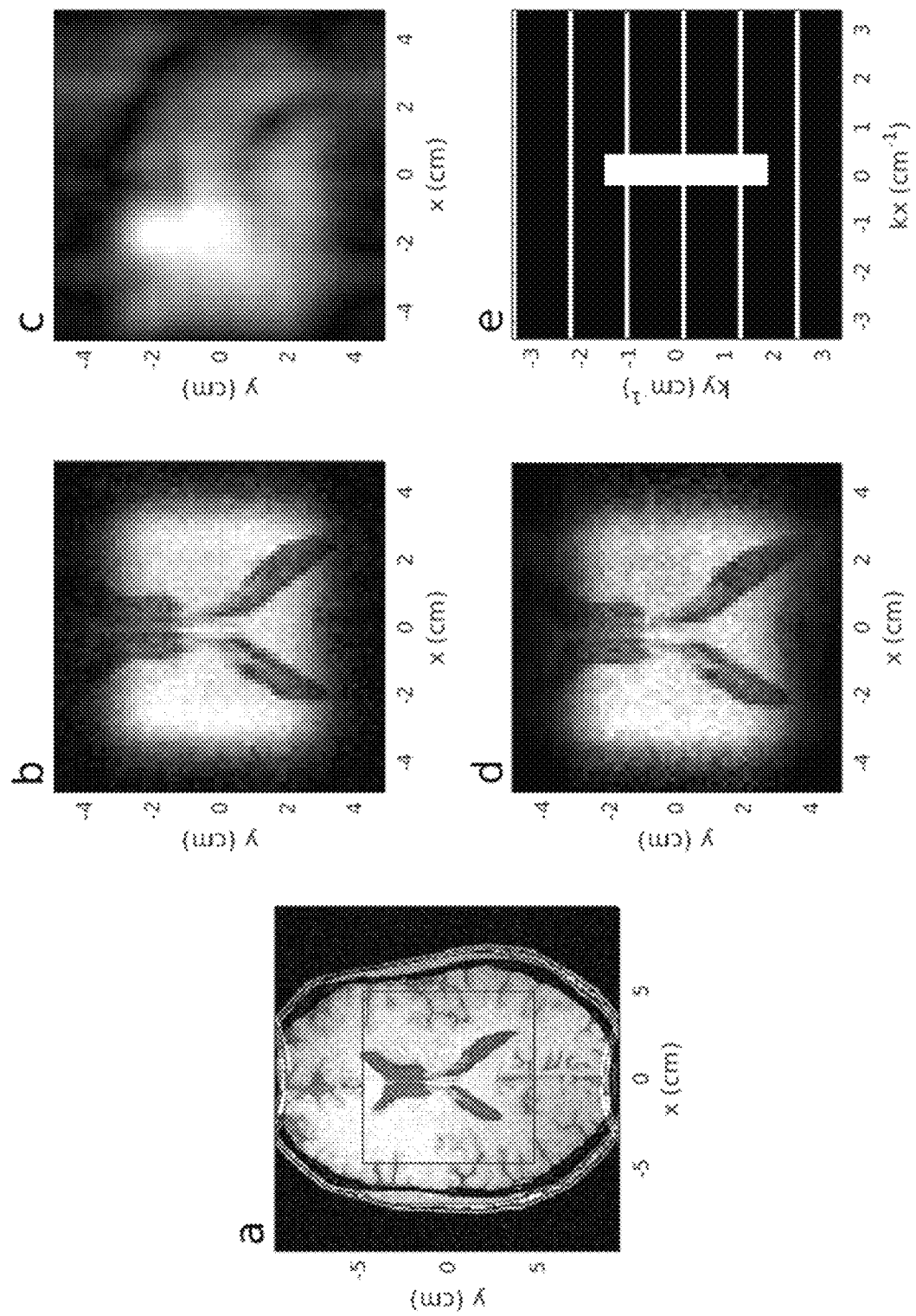
FIGS. 7A-7E show a single plane from the 3D reconstructions of the fully segmented 2D HS1 pulse. Sequence parameters were TR=6.09 ms, TE=2.76 ms, FA=10.4°, FOV=96×96×192 mm$^3$ with matrix size of 64×64×128.

In the fully segmented implementation, the pulse sequence parameters were TR=6.09 ms, TE=2.76 ms, FA=10.4 degrees, FOV=96×96×192 mm³ with matrix size 64×64×128. FIGS. 7A-7E show images obtained using this example sequence. FIG. 7A shows an image obtained with the sequence as described with non-selective excitation, FOV=192×192×192 mm³ and matrix size 192×192×192. The red box indicates the zoomed FOV in the phase encoded dimensions. FIG. 7B shows the reconstruction using the fully sampled dataset. FIG. 7C shows the reconstruction using only the undersampled data. FIG. 7D shows the image obtained using a GRAPPA reconstruction. FIG. 7E shows the undersampling pattern used.

Figures 8A, 8B, 8C, 8D, 8E:
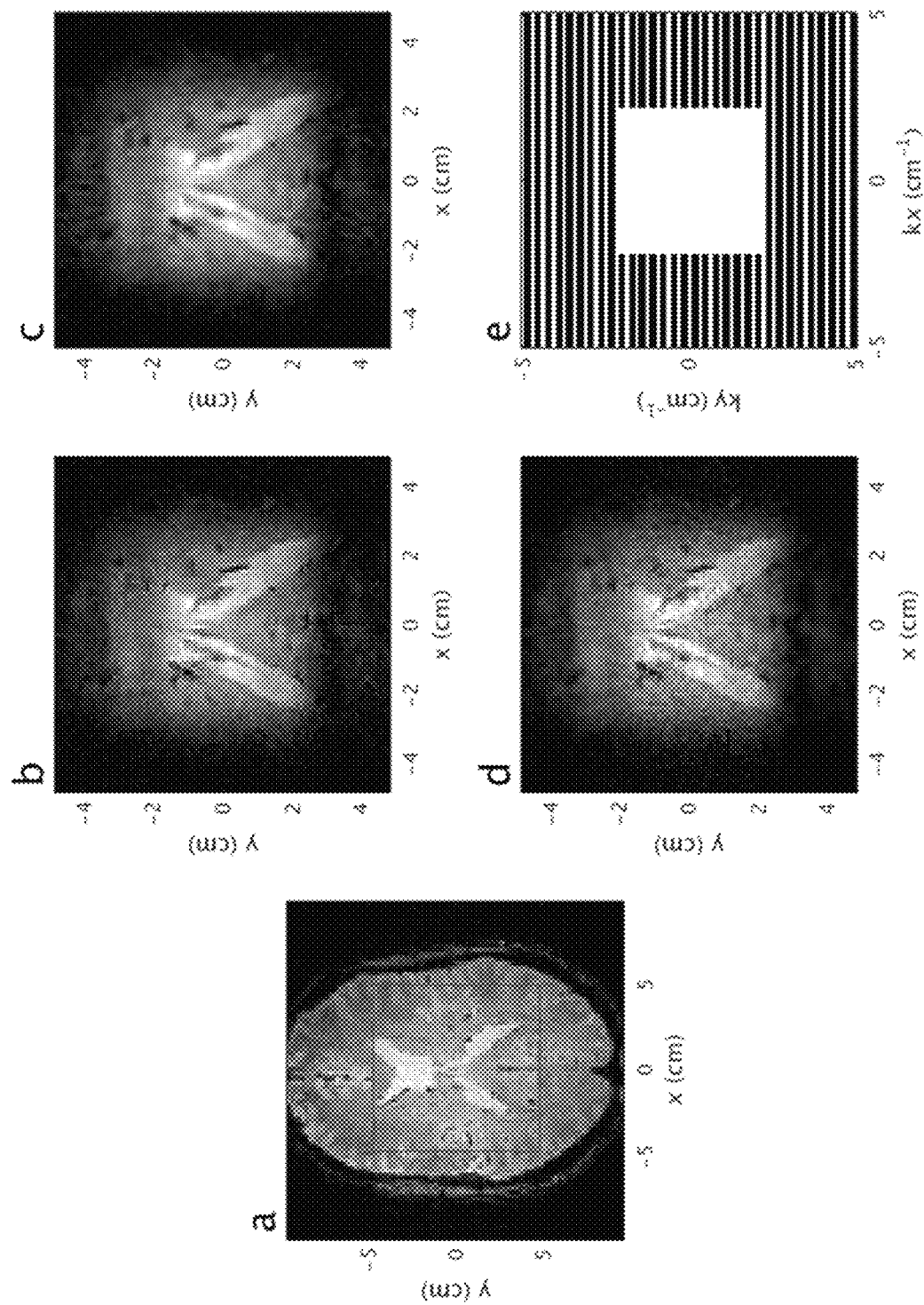
FIGS. 8A-8E a single plane from the 3D reconstructions of the 4-segment 2D HS1 pulse. Sequence parameters were $T_R$=41.5 ms, $T_E$=25 ms, flip angle=10°, FOV=96×96×192 mm$^3$ with matrix size of 96×96×192.

In the 4-segment implementation, the pulse sequence parameters were were TR=41.5 ms, TE=25 ms, FA=10 degrees, FOV=96×96×192 mm³ with matrix size 96×96×128. FIGS. 8A-8E show images obtained using this example sequence. FIG. 8A shows an image obtained with the sequence as described with non-selective excitation, FOV=192×192×192 mm³ and matrix size 192×192×192. The red box indicates the zoomed FOV in the phase encoded dimensions. FIG. 8B shows the reconstruction using the fully sampled dataset. FIG. 8C shows the reconstruction using only the undersampled data. FIG. 8D shows the image obtained using a GRAPPA reconstruction. FIG. 8E shows the undersampling pattern used.

In both cases, the GRAPPA kernel was 3×2×3 in $k_x$, $k_y$, and $k_z$, respectively. Every 11th line of $k_y$ was sampled on readout for the 28 segment pulse, with the central 10×20 lines of k-space fully sampled in the phase encoded dimensions, $k_x$ and $k_y$, for use as ACS lines. For the 4-segment pulse, the central 32 lines were employed as ACS lines, while every 2nd line was sampled along $k_y$ on acquisition. In both cases, the ACS lines were used in the final reconstruction. The acceleration per pulse segment with these sampling patterns are $R_{28}$=7.262 and $R_4$=1.959.

In this example implementation, the power for each segment in the 4-segment and the 28-segment pulse was set by comparing the RF amplitude (B1+) determined from Bloch simulation to an experimental RF power calibration.

In another example implementation, an echo-planar imaging ("EPI") gradient train was used during the excitation, and the low bandwidth achieved in the slow dimension of the pulses was increased by decreasing the pulse length of the RF pulse segments. Specifically, different segments of the pulse were undersampled to decrease the pulse length of each segment, thus increasing the bandwidth for a fixed time-bandwidth product, R. The direction of the oscillating (i.e., alternating) gradient in an EPI sequence can be referred to as the fast-selected dimension, while the direction of the blipped gradient can be referred to as the slow-selected dimension.

As a consequence of the amplitude modulation in the 2D HS1 pulse, each pulse segment will likely produce a different flip angle. As a result, under the commonly used acquisition condition TR<<T1, the different pulse segments may produce variable T1-weighting of the image data. This can be remedied by rescaling the power of each pulse segment to achieve a constant flip angle for all segments.

As part of the reconstruction process, at the end of all acquisitions, the data may be summed over all segments in either k-space or image space with the appropriate weights. During the summation over all segments used, perfect signal cancellation outside the desired selected region may not occur. This issue can be addressed by reweighting the reconstruction of each segment with a weight equal to the original flip angle of the segment. For a fully segmented pulse in which one line of k-space is sampled per segment, this procedure then amounts to reweighting each reconstruction according to a HS1 pulse defined by the number of segments used. For a partially segmented pulse, the data for each segment can be scaled in post-processing by the integral of the respective pulse segment. The weights can be given by Eqn. (10) above.

When undersampling a pulse, the sidebands in the slow dimension move closer to the baseband as the number of segments increases. The signals from these sidebands cancel after summing the acquired data. When a pulse segment is undersampled beyond the Nyquist limit, the sidebands and baseband overlap, which can lead to a non-uniform flip angle per segment. In these instances, despite maintaining the proper excitation region after summation, it may not be possible to obtain a consistent flip angle across the entire excitation region for each segment. However, when using a fully segmented pulse, such spatial variation of the flip angle in the slow dimension may not occur for the segments. In this limiting case, there may again be uniform T1 contrast within the desired profile. Rescaling the pulse amplitude to achieve the same flip angle for each segment gives equal SNR for each readout.

One or more images are then reconstructed from the acquired data, as indicated at step 108. As one example, images can be reconstructed using a GRAPPA or GRAPPA-like reconstruction. The determination of the GRAPPA weights may be an ill-posed linear inverse problem. In these instances, the problem can be regularized in order to find a unique solution that yields clinical-quality images.

As noted above, in most instances the transmitter is operated in a fixed mode, so there is no index over the transmit field map. In previous techniques such as TIAMO, the transmitter is not operated in a fixed mode, so the transmit field map varies between acquisitions. The role of the varying transmit field map in techniques such as TIAMO is replaced by the pulse segments in the methods described in the present disclosure in order to achieve spatial encoding. Additionally, the different excitation modes used in techniques such as TIAMO yield a varying flip angle between each excitation at a fixed spatial location. This non-ideality results in varying T1 weighting and SNR at the same spatial location for each transmit mode. The present approach maintains consistent T1 contrast and SNR with each excitation by using the same flip angle with every excitation segment. Additionally, the present approach can implement a complex summation over the excitation segments before combination of data from physical coils.

Figure 9:
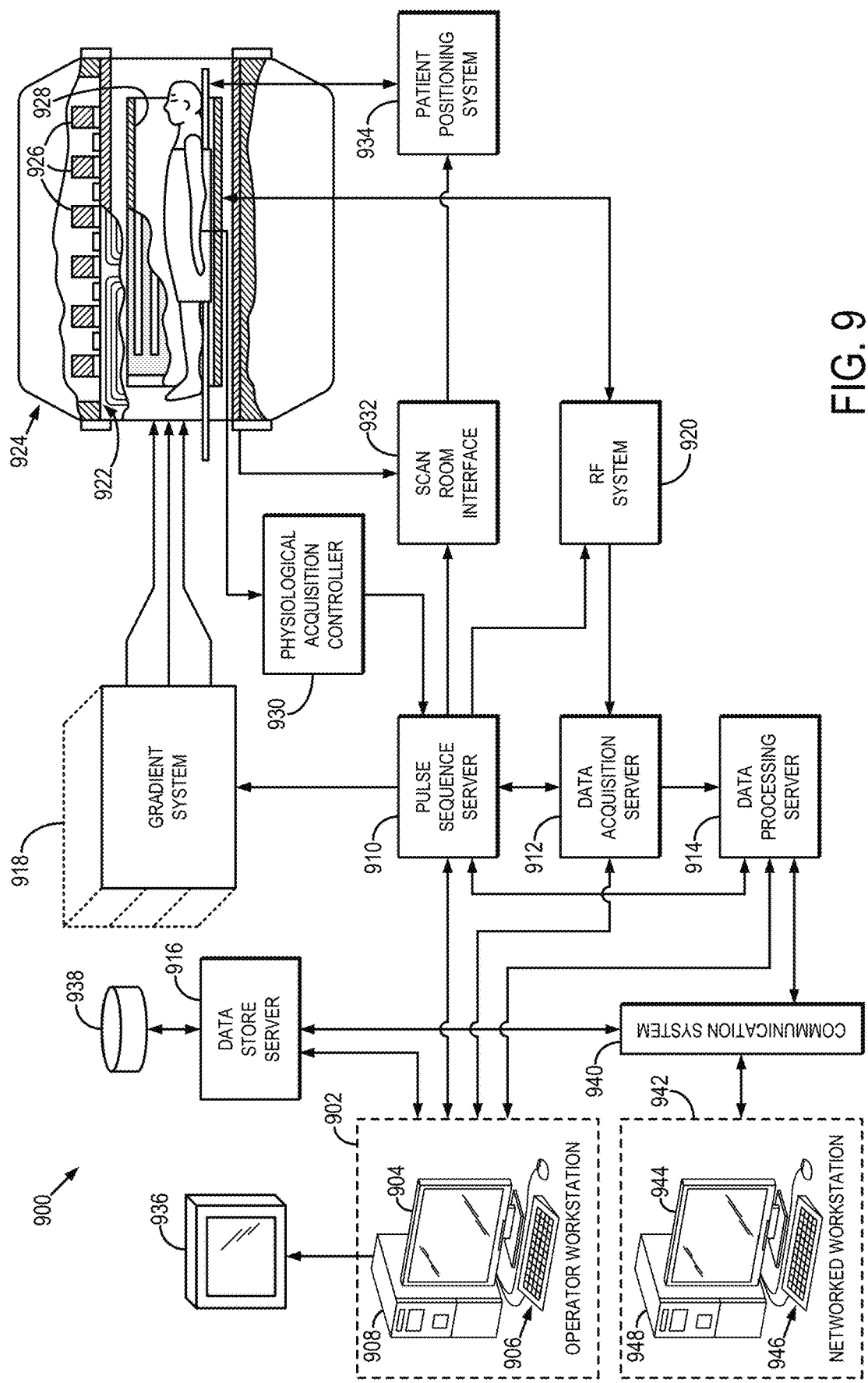
FIG. 9 is a block diagram of an example MRI system that can implement the methods described in the present disclosure.

Referring particularly now to FIG. 9, an example of an MRI system 900 that can implement the methods described here is illustrated. The MRI system 900 includes an operator workstation 902 that may include a display 904, one or more input devices 906 (e.g., a keyboard, a mouse), and a processor 908. The processor 908 may include a commercially available programmable machine running a commercially available operating system. The operator workstation 902 provides an operator interface that facilitates entering scan parameters into the MRI system 900. The operator workstation 902 may be coupled to different servers, including, for example, a pulse sequence server 910, a data acquisition server 912, a data processing server 914, and a data store server 916. The operator workstation 902 and the servers 910, 912, 914, and 916 may be connected via a communication system 940, which may include wired or wireless network connections.

The pulse sequence server 910 functions in response to instructions provided by the operator workstation 902 to operate a gradient system 918 and a radiofrequency ("RF") system 920. Gradient waveforms for performing a prescribed scan are produced and applied to the gradient system 918, which then excites gradient coils in an assembly 922 to produce the magnetic field gradients $G_x$, $G_y$, and $G_z$ that are used for spatially encoding magnetic resonance signals. The gradient coil assembly 922 forms part of a magnet assembly 924 that includes a polarizing magnet 926 and a whole-body RF coil 928.

RF waveforms are applied by the RF system 920 to the RF coil 928, or a separate local coil to perform the prescribed magnetic resonance pulse sequence. Responsive magnetic resonance signals detected by the RF coil 928, or a separate local coil, are received by the RF system 920. The responsive magnetic resonance signals may be amplified, demodulated, filtered, and digitized under direction of commands produced by the pulse sequence server 910. The RF system 920 includes an RF transmitter for producing a wide variety of RF pulses used in MRI pulse sequences. The RF transmitter is responsive to the prescribed scan and direction from the pulse sequence server 910 to produce RF pulses of the desired frequency, phase, and pulse amplitude waveform. The generated RF pulses may be applied to the whole-body RF coil 928 or to one or more local coils or coil arrays.

The RF system 920 also includes one or more RF receiver channels. An RF receiver channel includes an RF preamplifier that amplifies the magnetic resonance signal received by the coil 928 to which it is connected, and a detector that detects and digitizes the I and Q quadrature components of the received magnetic resonance signal. The magnitude of the received magnetic resonance signal may, therefore, be determined at a sampled point by the square root of the sum of the squares of the I and Q components:

$$M=\sqrt{I^2+Q^2} \tag{19}$$

and the phase of the received magnetic resonance signal may also be determined according to the following relationship:

$$\varphi = \tan^{-1}\left(\frac{Q}{I}\right). \tag{20}$$

The pulse sequence server 910 may receive patient data from a physiological acquisition controller 930. By way of example, the physiological acquisition controller 930 may receive signals from a number of different sensors connected to the patient, including electrocardiograph ("ECG") signals from electrodes, or respiratory signals from a respiratory bellows or other respiratory monitoring devices. These signals may be used by the pulse sequence server 910 to synchronize, or "gate," the performance of the scan with the subject's heart beat or respiration.

The pulse sequence server 910 may also connect to a scan room interface circuit 932 that receives signals from various sensors associated with the condition of the patient and the magnet system. Through the scan room interface circuit 932, a patient positioning system 934 can receive commands to move the patient to desired positions during the scan.

The digitized magnetic resonance signal samples produced by the RF system 920 are received by the data acquisition server 912. The data acquisition server 912 operates in response to instructions downloaded from the operator workstation 902 to receive the real-time magnetic resonance data and provide buffer storage, so that data is not lost by data overrun. In some scans, the data acquisition server 912 passes the acquired magnetic resonance data to the data processor server 914. In scans that require information derived from acquired magnetic resonance data to control the further performance of the scan, the data acquisition server 912 may be programmed to produce such information and convey it to the pulse sequence server 910. For example, during pre-scans, magnetic resonance data may be acquired and used to calibrate the pulse sequence performed by the pulse sequence server 910. As another example, navigator signals may be acquired and used to adjust the operating parameters of the RF system 920 or the gradient system 918, or to control the view order in which k-space is sampled. In still another example, the data acquisition server 912 may also process magnetic resonance signals used to detect the arrival of a contrast agent in a magnetic resonance angiography ("MRA") scan. For example, the data acquisition server 912 may acquire magnetic resonance data and processes it in real-time to produce information that is used to control the scan.

The data processing server 914 receives magnetic resonance data from the data acquisition server 912 and processes the magnetic resonance data in accordance with instructions provided by the operator workstation 902. Such processing may include, for example, reconstructing two-dimensional or three-dimensional images by performing a Fourier transformation of raw k-space data, performing other image reconstruction algorithms (e.g., iterative or backprojection reconstruction algorithms), applying filters to raw k-space data or to reconstructed images, generating functional magnetic resonance images, or calculating motion or flow images.

Images reconstructed by the data processing server 914 are conveyed back to the operator workstation 902 for storage. Real-time images may be stored in a data base memory cache, from which they may be output to operator display 902 or a display 936. Batch mode images or selected real time images may be stored in a host database on disc storage 938. When such images have been reconstructed and transferred to storage, the data processing server 914 may notify the data store server 916 on the operator workstation 902. The operator workstation 902 may be used by an operator to archive the images, produce films, or send the images via a network to other facilities.

The MRI system 900 may also include one or more networked workstations 942. For example, a networked workstation 942 may include a display 944, one or more input devices 946 (e.g., a keyboard, a mouse), and a processor 948. The networked workstation 942 may be located within the same facility as the operator workstation 902, or in a different facility, such as a different healthcare institution or clinic.

The networked workstation 942 may gain remote access to the data processing server 914 or data store server 916 via the communication system 940. Accordingly, multiple networked workstations 942 may have access to the data processing server 914 and the data store server 916. In this manner, magnetic resonance data, reconstructed images, or other data may be exchanged between the data processing server 914 or the data store server 916 and the networked workstations 942, such that the data or images may be remotely processed by a networked workstation 942.

The present disclosure has described one or more preferred embodiments, and it should be appreciated that many equivalents, alternatives, variations, and modifications, aside from those expressly stated, are possible and within the scope of the invention.

The invention claimed is:

1. A method for generating an image of a subject using a magnetic resonance imaging (MRI) system, the steps of the method comprising:
    (a) selecting with a computer system, a radio frequency (RF) pulse;
    (b) segmenting the RF pulse in order to generate a series of RF pulse segments;
    (c) acquiring data from a subject using an MRI system implementing a pulse sequence that includes the series of RF pulse segments; and
    (d) reconstructing an image of the subject from the acquired data using a reconstruction technique that treats the series of RF pulse segments as virtual receivers each having a virtual coil profile that is a product of an RF coil receive sensitivity, a transmit field map, and an excitation profile for each RF pulse segment.

2. The method as recited in claim 1, wherein the selected RF pulse is a two-dimensional RF pulse having a first dimension and a second dimension.

3. The method as recited in claim 2, wherein the RF pulse is a frequency-swept RF pulse in at least one of the first dimension and the second dimension.

4. The method as recited in claim 3, wherein the RF pulse is a frequency-swept RF pulse in both the first dimension and the second dimension.

5. The method as recited in claim 3, wherein the frequency-swept RF pulse is a hyperbolic secant RF pulse.

6. The method as recited in claim 2, wherein the selected RF pulse has a first bandwidth in the first dimension and a second bandwidth in the second dimension, and wherein the first bandwidth is larger than the second bandwidth.

7. The method as recited in claim 6, wherein the first dimension corresponds to a fast time direction and the second dimension corresponds to a slow time dimension in which the selected RF pulse is segmented into the series of RF pulse segments.

8. The method as recited in claim 7, wherein the second dimension corresponds to a phase-encoding direction.

9. The method as recited in claim 8, wherein the pulse sequence includes a series of phase-encoding gradient blips applied along the phase-encoding direction.

10. The method as recited in claim 8, wherein k-space is undersampled along the phase-encoding direction.

11. The method as recited in claim 2, wherein the second bandwidth is increased further by decreasing a pulse length of each RF pulse segment while maintaining a time-bandwidth product.

12. The method as recited in claim 1, wherein the each RF pulse segment corresponds to a group of k-space lines.

13. The method as recited in claim 12, wherein at least some groups of k-space lines corresponding to the RF pulse segments comprise k-space lines that are interleaved with k-space lines in other groups.

14. The method as recited in claim 1, wherein each RF pulse segment corresponds to a single k-space line.

15. The method as recited in claim 1, wherein the data are acquired using a single RF receive coil.

16. The method as recited in claim 1, wherein each RF pulse segment in the series of RF pulse segments has a peak RF amplitude that is scaled by a scaling factor in order to obtain a consistent flip angle across the series of RF pulse segments.

17. The method as recited in claim 16, wherein the pulse sequence used to acquire data in step (c) has a repetition time (TR) that is significantly shorter than a longitudinal relaxation time (T1) of tissues from which the data are acquired.

18. The method as recited in claim 16, wherein the scaling factor for each given RF pulse segment is computed as a mean value of a magnetization profile of that RF pulse segment.

\* \* \* \* \*